(12) United States Patent
Cheng et al.

(10) Patent No.: US 6,500,997 B2
(45) Date of Patent: Dec. 31, 2002

(54) CATALYSTS AND PROCESSES FOR THE CONVERSION OF AROMATIC HYDROCARBONS AND USES THEREOF IN THE PRODUCTION OF AROMATIC HYDROCARBONS

(75) Inventors: Wencai Cheng, Shanghai (CN); Dejin Kong, Shanghai (CN); Deqin Yang, Shanghai (CN); Huaying Li, Shanghai (CN); Zhirong Zhu, Shanghai (CN)

(73) Assignees: China Petro-Chemical Corporation (CN); Shanghai Research Institute of Petrochemical Engineering, Sinopec (CN)

( * ) Notice: Subject to any disclaimer, the term of this patent is extended or adjusted under 35 U.S.C. 154(b) by 0 days.

(21) Appl. No.: 09/090,917

(22) Filed: Jun. 5, 1998

(65) Prior Publication Data

US 2002/0091060 A1 Jul. 11, 2002

(30) Foreign Application Priority Data

| Jun. 6, 1997 | (CN) | 97106450 |
|---|---|---|
| Nov. 13, 1997 | (CN) | 97106716 |
| Nov. 13, 1997 | (CN) | 97106717 |
| Nov. 13, 1997 | (CN) | 97106718 |
| Nov. 13, 1997 | (CN) | 97106719 |

(51) Int. Cl.[7] .............................. C07C 5/22; C07C 5/52; B01J 29/18; B01J 29/06
(52) U.S. Cl. ..................... 585/475; 502/64; 502/73; 502/78; 502/65
(58) Field of Search .................. 502/64, 78, 65, 502/73; 585/475

(56) References Cited

U.S. PATENT DOCUMENTS

| 2,795,629 | A | | 6/1957 | Boedeker | |
| 3,527,825 | A | * | 9/1970 | Pollitzer | 585/474 |
| 3,551,510 | A | | 12/1970 | Pollitzer et al. | |
| 3,702,886 | A | * | 11/1972 | Argauer et al. | 423/705 |
| 3,729,521 | A | | 4/1973 | Gutberlet et al. | |
| 3,780,122 | A | | 12/1973 | Pollitzer | |
| 3,819,736 | A | | 6/1974 | Sato et al. | |
| 3,849,340 | A | | 11/1974 | Pollitzer | |
| 4,083,807 | A | * | 4/1978 | McKinney et al. | 208/120.2 |
| 4,158,026 | A | * | 6/1979 | Addison | 208/66 |
| 4,172,813 | A | | 10/1979 | Feinstein et al. | |
| 4,341,914 | A | | 7/1982 | Berger | |
| 4,414,138 | A | * | 11/1983 | Petty et al. | 502/73 |
| 4,665,258 | A | | 5/1987 | Butler et al. | |
| 4,668,655 | A | * | 5/1987 | Lewis et al. | 502/304 |
| 4,874,731 | A | | 10/1989 | Sachtler et al. | |
| 5,851,379 | A | * | 12/1998 | Innes et al. | 208/138 |

FOREIGN PATENT DOCUMENTS

| CN | 89106793.0 | | 3/1991 |
| JP | 49-46295 | | 12/1974 |
| JP | 51-29131 | | 8/1976 |
| JP | 7-185325 | * | 7/1995 |
| RU | 1 298 240 | | 3/1987 |

* cited by examiner

*Primary Examiner*—Stanley S. Silverman
*Assistant Examiner*—Christina Ildebrando
(74) *Attorney, Agent, or Firm*—Pennie & Edmonds LLP (57) ABSTRACT

The present invention relates a catalyst for the conversion of aromatic hydrocarbons, comprising by weight 20 to 90 parts of a crystalline aluminosilicate zeolite with a $SiO_2/Al_2O_3$ molar ratio of 10 to 100, 0.05 to 10 parts of metal bismuth or oxides thereof supported on the zeolite, 0 to 5 parts of one or more types of metal(s) M or oxides thereof, M being selected from the group consisting of molybdenum, copper, zirconium, strontium, lanthanum, rhenium, iron, cobalt, nickel and silver, and 10 to 60 parts of alumina as an adhesive. The present invention also relates to a process for the conversion of aromatic hydrocarbons using the catalyst of the present invention and uses thereof in the production of aromatic hydrocarbons.

15 Claims, 1 Drawing Sheet

Figure 1

CATALYSTS AND PROCESSES FOR THE CONVERSION OF AROMATIC HYDROCARBONS AND USES THEREOF IN THE PRODUCTION OF AROMATIC HYDROCARBONS

FIELD OF THE INVENTION

The present invention relates to catalysts and processes for the conversion of aromatic hydrocarbons and uses thereof in the production of aromatic hydrocarbons. In particular, the present invention relates to a novel catalyst comprising a zeolite with metal bismuth or oxides thereof supported thereon for the conversion of aromatic hydrocarbons, processes for the conversion of aromatic hydrocarbons using the catalyst, and uses thereof in the production of aromatic hydrocarbons.

BACKGROUND OF THE INVENTION

A large quantity of aromatic hydrocarbons such as benzene, toluene, xylene and $C_9$ aromatic hydrocarbons ($C_9$A) may be obtained from the reforming and cracking processes of the petroleum distillates. The contents of toluene and $C_9$A generally range from 40 to 50% of the total amount of the aromatic hydrocarbons dependent on different boiling ranges of the distillate feedstock and different processing methods. Normally $C_9$A, $C_{10}$ aromatic hydrocarbons ($C_{10}$ A) and aromatic hydrocarbons of more than ten carbon atoms are referred to as heavy aromatic hydrocarbons in the past. Heavy aromatic hydrocarbons are mainly derived from the side products of the cracking process of light oil for producing ethylene, the aromatic hydrocarbons extraction process in the catalytic reforming in refinery, as well as toluene disproportionation and transalkylation process. For various sources of the feedstock oil and different processing methods, an aromatic hydrocarbon combination unit of 225 thousand ton xylene output per year may produce 10 to 30 thousand tons of heavy aromatic hydrocarbons each year. $C_{10}$A and aromatic hydrocarbons of more than ten carbon atoms are of little use due to their complicated compositions and high boiling points. These aromatic hydrocarbons are not suitable for use as additive components in gasoline or diesel. Only some of them may be used as solvent oil or as the feedstock for separating durene, and most of the rest are used as burning fuel, causing waste of the resources.

With the development of plastic, synthetic fiber and synthetic rubber industries in the recent years, demand for benzene and xylene increases, market prices of which are higher than that of toluene and $C_9$A. It is an important research subject in many countries to increase the production of aromatic hydrocarbons of high value from less valuable aromatic hydrocarbons through conversion processes of aromatic hydrocarbons including hydrodealkylation, toluene disproportionation and transalkylation reactions, thus making full use of the aromatic hydrocarbon resources. Toluene disproportionation is a process in which one mole of benzene and one mole of xylene are produced from two moles of toluene. Toluene may undergo transalkylation reaction with $C_9$A to form xylene. Toluene may undergo transalkylation reaction with $C_{10}$A to form $C_9$A. Alkyl aromatic hydrocarbons such as $C_9$A and $C_{10}$A may undergo hydrodealkylation reaction to form aromatic hydrocarbons of fewer carbon atoms. A series of catalysts and processes for such reactions have already been developed.

In the processes for toluene disproportionation and transalkylation of the aromatic hydrocarbon feedstock substantially comprising toluene and $C_9$A, mordenite is frequently used as the catalyst. For example, U.S. Pat. Nos. 2,795,629, 3,551,510, 3,729,521; 3,780,122 and 3,849,340 disclose catalysts, feedstock compositions and reaction conditions for toluene disproportionation and transalkylation process, in which catalysts used are not mentioned to comprise bismuth. Japanese patent 49-46295 discloses a catalyst for preparing alkyl benzene, which comprises a mordenite with, supported thereon, a zirconium cocatalyst anid optionally one or more components selected from silver, bismuth, copper and lead. The catalysts in the above patents have restricted performances, thus can not resist stringent reaction conditions. Therefore, in the toluene disproportionation and transalkylation processes where the above catalysts are used, $C_9$A and heavy aromatic hydrocarbons of more than nine carbon atoms are not convertted adequately, hence yields of desired products relatively low, energy and material consumption on industrial scale units relatively high. So they are not economical.

Catalysts for converting $C_{10}$A and heavy aromatic hydrocarbons of more than ten carbon atoms have been reported. For example, Japanese patent publication 51-29131 discloses a catalyst, $MoO_3$—$NiO/Al_2O_3$ (13 wt % Mo, 5 wt % Ni) composition, and a process for treating $C_9$A and $C_{10}$A feedstock with this catalyst. U.S. Pat. No. 4,172,813 discloses a catalyst composition comprising 3 wt % $WO_3$, 5 wt % $MoO_3$ and a support consisting of 60 wt % mordenite and 40 wt % $Al_2O_3$; over this catalyst selective hydrodealkylation and transalkylation reactions of heavy reformate are effected, among which the main reaction is the transalkylation reaction between toluene and trimethylbenzene. U.S. Pat. No. 4,341,914 discloses a process for the conversion of $C_{10}$A. In these references no catalyst containing bismuth is mentioned, contents of $C_{10}$A in the feedstock entering the reactor is relatively low, no more than 20%, and the main disproportionation and transalkylation reaction is between toluene and $C_9$A.

SUMMARY OF THE INVENTION

Accordingly, one object of the present invention is to provide a novel catalyst for the conversion of aromatic hydrocarbons. The catalyst can be used in (1) disproportionation and transalkylation of aromatic hydrocarbon reactants comprising substantially toluene and $C_9$A and/or $C_{10}$A as well as in (2) hydrodealkylation and transalkylation of heavy aromatic hydrocarbons containing $C_9$A and/or aromatic hydrocarbons of more than nine carbon atoms. The catalyst has better catalytic capacity for various kinds of conversion reactions of aromatic hydrocarbons and can be employed under stringent reaction conditions. The catalyst increases the yields of desired products such as benzene and xylene. Thus, contents of heavy aromatic hydrocarbons in the aromatic reactants to be converted can be highly increased, allowing drying and pre-purifying procedures omitted or simplified. The catalyst can improve the conversion of heavy aromatic hydrocarbons, enhance the selectivity and yields of benzene and xylene, make full use of the $C_9$A and heavy aromatic hydrocarbon resources, lower material and energy consumption, and decrease expense.

Another object of the present invention is to provide a process for the conversion of aromatic hydrocarbons. The process overcomes the disadvantages of conventional disproportionation, transalkylation and hydrodealkylation processes that heavy aromatic hydrocarbons are restricted under a low content in the aromatic hydrocarbon reactants and that they are not suitable under stringent reaction conditions.

Still another object of the present invention is to apply said catalyst and process to the production of aromatic hydrocarbons, mainly benzene, xylene and $C_9A$.

The catalyst for the conversion of aromatic hydrocarbons according to the present invention comprises by weight 20 to 90 parts of a crystalline aluminosilicate zeolite with a $SiO_2/Al_2O_3$ molar ratio of 10 to 100, 0.05 to 10 parts of metal bismuth or oxides thereof supported on the zeolite, 0 to 5 parts of one or more types of metal(s) M or oxides thereof, M being selected from the group consisting of molybdenum, copper, zirconium, strontium, lanthanum, rhenium, iron, cobalt, nickel and silver, and 10 to 60 parts of alumina as an adhesive.

The present invention also provides a process for the conversion of aromatic hydrocarbons, in which the aromatic hydrocarbon reactants contact the catalyst of the present invention to effect the conversion reaction.

The present invention further relates to the use of the catalyst and process of the present invention for the conversion of aromatic hydrocarbons in the production of aromatic hydrocarbons such as benzene, xylene and $C_9A$ from toluene, $C_9A$, $C_{10}A$ and aromatic hydrocarbons of more than ten carbon atoms.

DETAILED DESCRIPTION OF THE INVENTION

1. Catalyst of the Present Invention for the Conversion of Aromatic Hydrocarbons and Its Preparation The catalyst according to the present invention for the conversion of aromatic hydrocarbons comprises by weight 20 to 90 parts of a crystalline aluminosilicate zeolite with a $SiO_2/Al_2O_3$ molar ratio of 10 to 100, 0.05 to 10 parts of metal bismuth or oxides thereof supported on the zeolite, 0 to 5 parts of one or more types of metal(s) M or oxides thereof, M being selected from the group consisting of molybdenum. copper, zirconium, strontium, lanthanum, rhenium, iron, cobalt, nickel and silver. and 10 to 60 parts of alumina as an adhesive.

The catalyst of the present invention may be prepared by weighing the starting materials in amounts corresponding to the predetermined composition of the final product, said starting materials including zeolite, metal bismuth or its compound, metal(s) M or oxides thereof, M being selected from the group consisting of molybdenum, copper, zirconium, strontium, lanthanum, rhenium, iron, cobalt, nickel and silver, and alumina, mixing the starting materials thoroughly, followed by extruding, drying, pelleting and calcining for activating.

The zeolite used may be natural or synthesized. Non-limiting examples of the. zeolite include mordenite, ZSM-5 zeolite and β-zeolite or a mixture thereof, preferably mordenite, and more preferably hydrogen-form mordenite.

The $SiO_2$-to-$Al_2O_3$ molar ratio of the zeolite is within the range from 10 to 100, for example 10 to 30.

In one preferred embodiment hydrogen-form mordenite with a sodium content less than 0.2 wt % is used, which mordenite may be a aluminum-lean mordenite prepared by extracting aluminum from low silica mordenite with an inorganic acid, or a hydrogen-form mordenite prepared by ion-exchanging the direct-crystallized high silica Na-mordenite with ammonium chloride or nitrate solution.

Non-limiting examples of bismuth compounds are bismuth oxide and bismuth nitrate, preferably bismuth nitrate.

Non-limiting examples of metal M compound(s) may be oxide(s) or salt(s) thereof, such as M nitrate. When M comprises molybdenum, the molybdenum compound in the starting material may take the form of ammonium molybdate.

Said mixing procedure may be carried out by kneading the starting materials or impregnating the solid materials with an aqueous solution. Said extruding, drying, pelleting and calcining procedures may be proceeded by traditional methods in the prior art.

2. Process for the Conversion of Aromatic Hydrocarbons According to the Present Invention

The present invention provides processes for the conversion of aromatic hydrocarbons, in which the aromatic hydrocarbon reactants contact the novel catalyst of the present invention to effect the conversion reactions.

The reaction conditions in said processes may be as follows:

In the presence of hydrogen, the aromatic hydrocarbon reactants flow through a gas-solid fixed bed reactor and contact the catalyst inside at a reaction temperature within the range from 300 to 600° C., a reaction pressure within the range from 1.5 to 4.0 MPa, an aromatic hydrocarbon reactant weight hourly space velocity within the range from 0.5 to 3.0 $hr^{-1}$ and a hydrogen-to-hydrocarbon molar ratio within the range from 2 to 10.

The aromatic hydrocarbon reactants comprise one or more aromatic hydrocarbons selected from toluene, $C_9A$, $C_{10}A$ and aromatic hydrocarbons of more than ten carbon atoms or mixtures thereof, may contain a certain amount of impurities, such as water, indane, trace naphthalene, methylnaphthalene, dimethylnaphthalene and non-aromatic compounds. The aromatic hydrocarbon reactants contact the novel catalyst of the present invention under the reaction conditions and there may mainly occur the following reactions:

(1) Toluene Disproportionation Reaction:

(2) Hydrodealkylation Reactions of Aromatic Hydrocarbons:

(3) Transalkylation Reactions of Aromatic Hydrocarbons:

Conventional processes for toluene disproportionation and transalkylation from toluene and $C_9A$ reactants are carried out in a fixed bed reactor in the presence of hydrogen and a mordenite catalyst to produce $C_6$~$C_{10}A$, $C_1$~$C_5$ alkanes and a small amount of $C_{11}$ aromatic hydrocarbons ($C_{11}A$). Toluene and $C_9A$ in the reaction zone effluent are separated, recycled, and combined with fresh toluene and $C_9A$ outside to enter the reactor as feedstock. In toluene disproportionation and transalkylation processes or hydrodealkylation processes, heavy aromatic hydrocarbons, especially $C_{10}A$ and aromatic hydrocarbons of more than ten carbon atoms, may undergo accompanying side reactions such as (1) hydrocracking reactions to form saturated hydrocarbons and (2) aromatic condensation reactions to form polycyclic or fused ring compounds. The higher the reaction temperature is, the more serious the side reactions are, the more large molecule condensation products are formed, the more coke deposits on the catalyst and the quicker the activity of the catalyst decreases. $C_{10}A$ fraction contains trace polycyclic compounds such as naphthalene, methylnaphthalene and dimethylnaphthalene, which readily deactivate the catalyst. Therefore, as for the conversion reactions such as disproportionation and transalkylation of aromatic hydrocarbons, in order to slow the coke deposit rate on the catalyst and prolong catalyst life, it is required to run the reactions in the presence of hydrogen and to limit $C_{10}A$ contents in the aromatic hydrocarbon reactants to generally less than 4%, at the most no higher than 8%, and less than 2% in industrial practices. Indane is a poison to the catalyst for disproportionation and transalkylation reactions and usually controlled at less than 0.5%. The known catalysts for disproportionation and transalkylation reactions are of limited performances and can not be used for treating reactants containing high contents of $C_{10}A$ and aromatic hydrocarbons of more than ten carbon atoms. Since the boiling point of indane is very close to that of trimethylbenzene (TMB) in $C_9A$, and the indane content in $C_9A$ from the top of the heavy aromatic hydrocarbon tower which provides fresh $C_9A$ for the disproportionation unit, generally must be less than 1.0% so as to meet the processing requirements, about 5~15% of $C_9A$ from the tower bottom of the heavy aromatic hydrocarbon tower is removed and can not be fully utilized.

It is surprising that the bismuth-containing zeolite catalyst of the present invention has much better catalytic properties than known catalysts. Not only does it loosen the limit for the indane content in the reaction feedstock so that the indane content may be up to 0~5 wt % of the reaction feedstock and thereby it is no longer compulsory to remove most of the indane from the starting feedstock through heavy aromatic hydrocarbon tower, thus loss of $C_9A$ during separating indane is avoided; but also does it have stronger catalytic capacity for hydrodealkylation and transalkylation reactions of $C_{11}$ and $C_{10}A$ and can resist the poisonous impurities in heavy aromatic hydrocarbon feedstock, so that $C_{10}A$ can be passed into the reactor or recycled as feedstock instead of being removed from the heavy aromatic hydrocarbon tower bottom, so the utilization ratio of the heavy aromatic hydrocarbons increases, effecting good results.

Hence, in the process of the present invention for the conversion of aromatic hydrocarbons, the aromatic hydrocarbon reactants may comprise substantially a mixture of toluene and $C_9A$ in which the weight ratio of toluene to $C_9A$ is within the range from 90/10 to 10/90.

In the process of the present invention for the conversion of aromatic hydrocarbons, the aromatic hydrocarbon reactants may comprise substantially heavy aromatic hydrocarbons, such as $C_9A$, $C_{10}A$ and aromatic hydrocarbons of more than ten carbon atoms or a mixture thereof.

In the process of the present invention for the conversion of aromatic hydrocarbons, the aromatic hydrocarbon reactants may comprise substantially a mixture of toluene, $C_{10}A$ and aromatic hydrocarbons of more than ten carbon atoms, in which the weight ratio of toluene to $C_{10}A$ is within the range from 90/10 to 10/90.

It is also surprising that, for the catalyst of the present invention, water content in the reactant mixture is not required to be very low. In U.S. Pat. No. 3,780,122, water content in the toluene feedstock has remarkable effect on the activity and stability of the catalyst for the toluene disproportionation reaction; even very low water content (15 ppm) can influence the toluene conversion. In this patent water content in toluene is required to be less than 25 ppm. U.S. Pat. No. 4,665,258 (1987) provides a novel improved toluene disproportionation process, in which aluminum-lean mordenite is used as a catalyst, can be carried out under stringent reaction conditions. The mordenite used in this catalyst is of a silica-to-alumina molar ratio more than 30, preferably within the range from 40 to 60. Feedstock of more than 25 ppm water content may be directly passed into the reaction zone; yet permitted water content may be within the range from 50 and 250 ppm. In the process of the present invention, the bismuth-containing zeolite catalyst used has substantially improved water resistance and can even maintain high activity and stability when the feedstock contains up to 500 ppm water. For an industrial scale unit the dehydrating procedure for the feedstock can therefore be omitted or simplified. In addition, the high activity of the present catalyst can achieve a hydrocarbon conversion ratio of, for example, up to 45% at a low reaction temperature, meanwhile preserving excellent stability, effecting very good results.

Therefore, in the process of the present invention for the conversion of aromatic hydrocarbons, water content in the aromatic hydrocarbon reactants may be up to 500 ppm.

3. Use of the Catalyst and Process of the Present Invention in the Production of Aromatic Hydrocarbons By the process of the present invention for the conversion of aromatic hydrocarbons, benzene and toluene may be produced from feedstock substantially comprising toluene and $C_9A$; and benzene, xylene and $C_9A$ may be produced from feedstock containing toluene, $C_{10}A$ and aromatic hydrocarbons of more than ten carbon atoms. A small amount of $C_1$~$C_4$ aliphatic hydrocarbons may be formed in each case above. Thereby, the process of the present invention may be applied to the production of benzene, xylene and $C_9A$ from feed materials of various complex compositions.

One embodiment of applying the process of the present invention to the production of benzene and xylene comprises the following steps of:
(a) separating an aromatic feedstock comprising indane, $C_8$ aromatic hydrocarbons ($C_8A$), $C_9A$, $C_{10}A$ and $C_{11}$ aromatic hydrocarbons ($C_{11}A$) in a first separation zone comprising a first and a second separation tower, where a stream rich in $C_8A$ is separated from the top of the first separation tower and the bottoms product of the first tower is passed into the second separation tower, where a stream comprising indane, $C_9A$ and $C_{10}A$, with an indane content of 0 to 5 wt % and a $C_{10}A$ content of 0 to 50 wt %, is separated from the top of the second separation tower and $C_{11}A$ are removed from the second tower bottom;
(b) passing the effluent stream from the top of the second separation tower along with toluene into a conversion reaction zone for the aromatic hydrocarbons, where said reaction zone is packed with the catalyst of the present invention, and the aromatic hydrocarbons are transformed, upon contacting the catalyst under conversion conditions, into a converted effluent rich in benzene and $C_8A$; and
(c) passing said converted effluent into a second separation zone and separating them into benzene, toluene, $C_8A$ and heavy aromatic hydrocarbons containing $C_{10}A$.

According to the above embodiment, toluene separated from the second separation zone can be fed into the reaction zone. A part of benzene separated from the second separation zone can be recycled into the reaction zone to increase $C_8A$ yield; however, it may be removed directly as a product instead of being recycled because recycling of benzene will lower the conversion ratio of feed toluene. The heavy aromatic hydrocarbons containing $C_{10}A$ separated from the second separation zone may be passed into the second separation tower of the first separation zone with or without o-xylene separated therefrom. In the feed stream entering into the conversion reaction zone, the weight ratio of toluene to $C_9A$ is within the range from 90/10 to 10/90.

By employing the novel catalyst of the present invention, limit to indane content in the aromatic feedstock is loosened, allowing it to range from 0 to 5 wt %. Therefore, it is not compulsory to separate and remove a major part of indane, which is of small amount, accompanied by the $C_9A$ feedstock through the heavy aromatic hydrocarbon tower, hence loss of $C_9A$ in indane separation process can be eliminated. Since the catalyst of the present invention enjoys strong capacity of converting $C_{10}A$, $C_{10}A$ per se may be recycled and it is no longer necessary to remove them from the heavy aromatic hydrocarbon tower bottom, thus increasing $C_{10}A$ utilization ratio.

Figure 1:
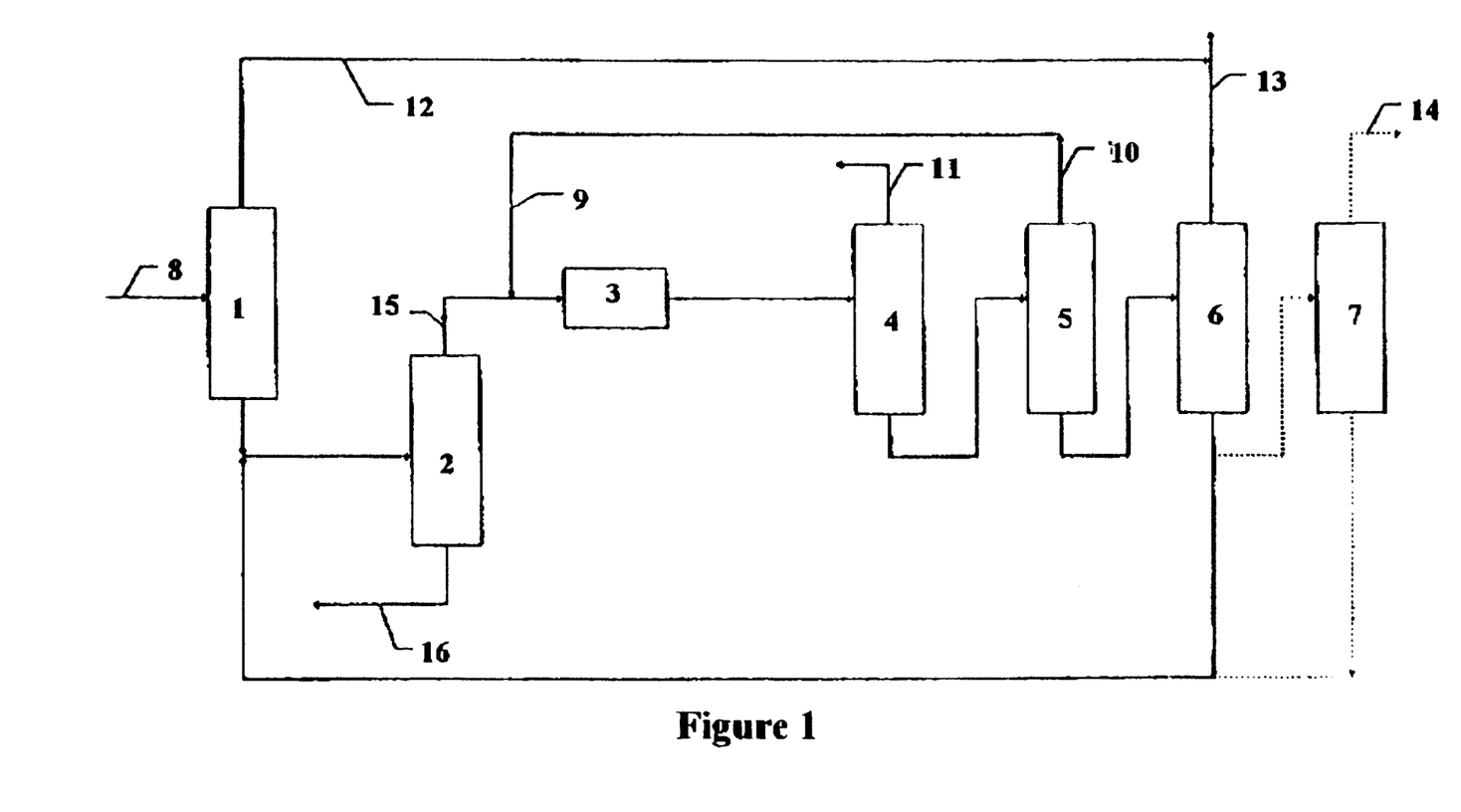
FIG. 1 is a schematic diagram of a preferred embodiment of the use of the process of the present invention in the production of aromatic hydrocarbons.

The process represented by FIG. 1 comprises a first separation zone, a second separation zone and an aromatic hydrocarbon conversion reaction zone 3. The first separation zone comprises an xylene tower 1 and a heavy aromatic hydrocarbon tower 2. The second separation zone comprises a benzene tower 4, a toluene tower 5 and an xylene tower 6 and/or an o-xylene tower 7. The reaction zone includes a reactor, a high pressure separation tank and a stripping tower. The effluent of the reaction zone, which contains $C_6 \sim C_{11}A$, is first passed into the benzene tower 4, where a product stream 11 rich in benzene is separated and removed or partially recycled into the reaction zone. The tower bottoms product of the benzene tower 4 is passed into the toluene tower 5. The toluene recycle stream 10 from the top of the toluene tower 5 is passed into the reaction zone along with fresh toluene, and the tower bottoms product of the toluene tower 5 is passed into the xylene tower 6. The stream 13 separated from the xylene tower 6, a mixture of ethylbenzene, m-xylene and p-xylene, is combined with stream 12 rich in $C_8A$ from the top of the xylene tower 1 and removed from the system. The tower bottoms products of the xylene tower 6 may be combined with the tower bottoms product of the xylene tower 1 which is rich in $C_9A$ and indane, and passed into the heavy aromatic hydrocarbon tower 2. Or, the tower bottoms product of xylene tower 6 may be first passed into an o-xylene tower 7 to separate therefrom a stream 14 rich in o-xylene stream, then combined with the tower bottoms product of the xylene tower 1 and then passed into the heavy aromatic hydrocarbon tower 2. A stream 15 separated from the top of the heavy aromatic hydrocarbon tower 2, rich in $C_9A$, $C_{10}$ hydrocarbons and containing all indane brought in, is fed into the reaction zone, while the tower bottoms effluent stream 11 rich in $C_{11}A$, is removed from the system. The $C_{10}$ hydrocarbons in the stream from the top of the heavy aromatic hydrocarbon tower of this process comprise $C_{10}A$, $C_{10}$ cyclic hydrocarbons and $C_{10}$ fused ring hydrocarbons.

Other advantages and features of the present invention will be apparent upon reading the following non-limiting examples.

EXAMPLES

I. Catalysts for the Conversion of Aromatic Hydrocarbons

Example 1

77.8 g of an ammonium-form mordenite ($Na_2O$ content: less than 0.15%, $SiO_2/Al_2O_3$ molar ratio: 12, weight loss after calcination at 550° C.: 30%) powder was mixed thoroughly with 42.9 g of pseudoboehmite ($\alpha$-$Al_2O_3 \cdot H_2O$, $Na_2O$ content: less than 0.15%, weight loss after calcination at 550° C.: 30%). 0.10 g of bismuth nitrate [$Bi(NO_3)_3 \cdot 5H_2O$, chemically pure], 2 ml of nitric acid (chemically pure), 60 ml of water, 5.77 g of ammonium molybdate [$(NH_4)_6Mo_7O_{24}$, chemically pure] were mixed to prepare a solution. This solution was added into the mixture of ammonium-form mordenite and pseudoboehmite, and the resultant mixture was mixed and kneaded thoroughly, extruded into strips, dried by oven, pelleted and calcined for activating to yield a catalyst A, the $Bi_2O_3/MoO_3/H$-mordenite/$Al_2O_3$ weight ratio of which was 0.05/5/70/30.

Example 2

44.4 g of an ammonium-form mordenite powder and 85.7 g of pseudoboehmite in example 1 were mixed thoroughly. 0.14 g of bismuth nitrate [$Bi(NO_3)_3 \cdot 5H_2O$, chemically pure], 0.58 g of ammonium molybdate [$(NH_4)_6Mo_7O_{24}$, chemically pure], 19.4 g of nickel nitrate [$Ni(NO_3)_2 \cdot 6H_2O$, chemically pure], 1.5 ml of nitric acid (chemically pure) and 60 ml of water were mixed to prepare a solution. This solution was added into the mixture of ammonium-form mordenite and pseudoboehmite, and the resultant mixture was mixed and kneaded thoroughly, extruded into strips, dried by oven, pelleted and calcined for activating to yield a catalyst B, the $Bi_2O_3/MoO_3/NiO/H$-mordenite/$Al_2O_3$ weight ratio of which was 0.07/0.5/5.0/40/60.

Example 3

55.6 g of an ammonium-form mordenite ($Na_2O$ content: less than 0.15%, $SiO_2/Al_2O_3$ molar ratio: 26.1, weight loss after calcination at 550° C.: 10%) powder was mixed with 71.4 g of pseudoboehmite of the same type in example 1. 10.4 g of bismuth nitrate [$Bi(NO_3)_3 \cdot 5H_2O$, chemically pure], 2.1 ml of nitric acid (chemically pure), 50 ml of water were mixed to prepare a solution. This solution was added into the mixture of ammonium-form mordenite and pseudoboehmite, and the resultant mixture was mixed and kneaded thoroughly, extruded into strips, dried by oven, pelleted and calcined for activating to yield a catalyst C, the $Bi_2O_3/H$-mordenite/$Al_2O_3$ weight ratio of which was 5/50/50.

Example 4

66.7 g of an ammonium-form mordenite ($Na_2O$ content: less than 0.15%, $SiO_2/Al_2O_3$ molar ratio: 19.2, weight loss after calcination at 550° C.: 10%) was mixed thoroughly with 57.1 g of pseudoboehmite of the same type in example 1. 1.88 g of bismuth nitrate [$Bi(NO_3)_3 \cdot 5H_2O$, chemically pure], 3.88 g of nickel nitrate [$Ni(NO_3)_2 \cdot 6H_2O$, chemically pure], 1.8 ml of nitric acid (chemically pure) and 55 ml of water were mixed to prepare a solution. This solution was added into the mixture of ammonium-form mordenite and pseudoboehmite, and the resultant mixture was mixed and kneaded thoroughly, extruded into strips, dried, pelleted and calcined for activating to yield a catalyst D, the $Bi_2O_3/NiO/H$-mordenite/$Al_2O_3$ weight ratio of which was 0.9/0.1/60/40.

Example 5

A ZSM-5 zeolite with a $SiO_2/Al_2O_3$ molar ratio of 65 was synthesized by the method described in U.S. Pat. No. 3,702,886(1972), calcined at 550° C. for 2 hours under nitrogen atmosphere, then ion-exchanged with ammonium chloride or nitrate solution at 80~98° C. for 1~10 hours, filtered to remove the mother liquor, then ion-exchanged repetitively for several times, washed with deionized water, and dried by oven at 110° C. to yield a H-ZSM-5 zeolite, the $Na_2O$ content of which was less than 0.1 wt %.

H-ZSM-5 zeolite and pseudoboehmite ($\alpha$-$Al_2O_3 \cdot H_2O$) were mixed at a weight ratio of 70/30, added with dilute nitric acid, bismuth nitrate and water, kneaded thoroughly, extruded into strips, dried by oven at 110° C., pelleted and calcined at 560° C. for 4 hours to yield a catalyst E, the $Bi_2O_3$ content of which was 1.0 wt %.

Example 6

A catalyst F was prepared in the same manner as in example 5 except that a commercial $\beta$-zeolite ($SiO_2/Al_2O_3$ molar ratio: 35.0) was used in place of the synthesized ZSM-5 zeolite. Catalyst F is a bismuth-containing $\beta$-zeolite catalyst, the $Bi_2O_3$ content of which was 1.0 wt %.

Example 7 (Comparative Example)

A catalyst Ec, a ZSM-5 zeolite catalyst containing no bismuth, was prepared in the same manner as in example 5 except that no bismuth nitrate was added.

Example 8 (Comparative Example)

A catalyst Fc, a $\beta$-zeolite catalyst containing no bismuth, was prepared in the same manner as in example 6 except that no bismuth nitrate was added.

Example 9

A high-silica H-mordenite zeolite was synthesized from a high-silica Na-mordenite, which was of a $SiO_2/Al_2O_3$ molar ratio of 15~30 and prepared according to the method described in the Chinese patent ZL 89106793.0, by ion-exchanging with ammonium chloride or nitrate solution at 90~98° C. for 1~8 hours and filtering to remove the mother liquor, then ion-exchanging repetitively for several times, washing, and drying by oven at 110° C. to obtain a high-silica H-mordenite.

The high-silica H-mordenite and pseudoboehmite ($\alpha$-$Al_2O_3 \cdot H_2O$) were mixed, added with dilute nitric acid, bismuth nitrate and water, kneaded thoroughly, extruded into strips, dried by oven at 110° C., pelleted and calcined at 580° C. to yield a catalyst G1, the $Bi_2O_3$ content of which was 0.1 wt %. Catalysts G2, G3, G4, G5 and G6, with different contents of mordenite, alumina and $Bi_2O_3$ as shown in Table 6, were prepared respectively in the same manner by varying the amounts of pseudoboehmite and bismuth nitrate used.

Example 10

A high-silica H-mordenite and a commercial pseudoboehmite ($\alpha$-$Al_2O_3 \cdot H_2O$) were mixed, added with dilute nitric acid and water, kneaded thoroughly, extruded, dried by oven at 110° C., pelleted and calcined at 400° C. to yield cylinder particles. The cylinder particles were impregnated with bismuth nitrate aqueous solution over night, dried by oven at 110° C., and calcined at 540° C. to yield a catalyst H1, the $Bi_2O_3$ content of which was 0.1 wt %. Catalysts H2, H3, H4 and H5, compositions of which were shown in Table 6, containing $Bi_2O_3$, respectively, 0.5, 1.0, 5.0, 10.0 wt %, were prepared correspondingly in the same manner by varying the amount of bismuth nitrate used.

Example 11

In this example, a bismuth-containing aluminum-lean mordenite catalyst was prepared.

An aluminum-lean mordenite was synthesized as follows:

A commercial Na-mordenite with a $SiO_2/Al_2O_3$ molar ratio of 10 was refluxed with dilute nitric acid solution at 90° C. to extract aluminum from the mordenite, filtered, washed, and dried to obtain an aluminum-lean mordenite with a $SiO_2/Al_2O_3$ molar ratio of 15.1, referred to hereinafter as aluminum-lean mordenite zeolite HM-15.1. The dealuminating procedure was repeated several times for HM-15.1 to obtain aluminum-lean mordenite zeolites with $SiO_2/Al_2O_3$ molar ratios of 19.8 and 24.9, referred to hereinafter as HM-19.8 and HM-24.9 respectively.

Catalysts I1, I2 and I3 were prepared in the same manner as in example 9 except that HM-15.1, HM-19.8 and HM-24.9 were respectively used in place of the high silica H-mordenite zeolite.

Example 12 (Comparative Example)

A catalyst J, a mordenite zeolite catalyst containing no bismuth, was prepared in the same manner as in example 9 except that no bismuth nitrate was added.

Example 13

High-silica H-mordenite and commercial pseudoboehmite ($\alpha$-$Al_2O_3 \cdot H_2O$) were mixed, added with dilute nitric acid, water, bismuth nitrate and lanthanum nitrate, kneaded thoroughly, extruded into strips, dried by oven at 110° C., pelleted and calcined at 500° C. to yield a catalyst K1, the $Bi_2O_3$ content of which was 0.1 wt %. Catalysts K2, K3, K4 and K5, compositions of which were shown in Table 8, containing $Bi_2O_3$ and an oxide of copper, zirconium, rhenium or strontium were prepared respectively in a similar manner.

II. Process of the Present Invention for the Conversion of Aromatic Hydrocarbons Catalysts prepared in the above examples were employed in the conversion processes for aromatic hydrocarbons in the following examples.

(1) Where the Aromatic Hydrocarbon Reactants Comprise Substantially Toluene and $C_9A$

Example 14~17

A cylinder stainless steel reactor with an inner diameter of 25 mm, a length of 1000 mm was used. 20 g of catalyst G3 of example 9 were packed inside the reactor to form a catalyst bed, on top of which and below which were filled with glass beads of 5 mm diameter for the purposes of gas stream distribution, supporting the bed, preheating and vaporizing the feedstock. The feed toluene and $C_9A$ were derived from the aromatic hydrocarbon combination unit in petrochemical industry. The feedstock was mixed with hydrogen and passed through the catalyst bed from the top to the bottom. The hydrogen used was obtained from electrolysis. The reactor was heated electrically and the reaction temperature was controlled automatically.

Feedstock compositions, catalysts used, reaction conditions and experimental results were summarized in Table 1.

TABLE 1

Reaction Conditions and Results for
Feedstock Rich in Toluene and $C_9A$

| Example | 14 | 15 | 16 | 17 |
|---|---|---|---|---|
| Catalyst | G3 | G3 | G3 | G3 |
| Temperature, °C. | 300 | 380 | 420 | 480 |

TABLE 1-continued

Reaction Conditions and Results for Feedstock Rich in Toluene and $C_9A$

| Example | 14 | 15 | 16 | 17 |
|---|---|---|---|---|
| Pressure, MPa | 2.0 | 3.0 | 3.0 | 4.0 |
| WHSV, $hr^{-1}$ | 0.8 | 2.0 | 3.0 | 4.5 |
| Hydrogen/Hydrocarbon Molar Ratio | 1 | 5 | 10 | 15 |
| Feedstock Composition, % | | | | |
| $C_1$~$C_5$ Non-aromatic Hydrocarbons | / | / | / | / |
| Benzene | 0.27 | / | / | / |
| Toluene | 90.30 | 58.30 | 40.30 | 10.50 |
| $C_8A$ | 1.31 | 1.10 | 0.70 | 0.50 |
| $C_9$ Non-aromatic Hydrocarbons | / | 1.00 | 1.07 | 1.10 |
| $C_9A$ | 5.41 | 35.02 | 49.80 | 70.40 |
| $C_{10}$ Hydrocarbons | 2.51 | 3.50 | 5.90 | 13.50 |
| Indane | 0.20 | 1.08 | 2.23 | 4.00 |
| Product Effluent Composition, % | | | | |
| $C_1$~$C_5$ Non-aromatics | 0.52 | 1.04 | 1.20 | 1.33 |
| Benzene | 17.42 | 9.26 | 9.26 | 3.26 |
| Toluene | 52.37 | 52.37 | 36.92 | 20.24 |
| Ethylbenzene | 1.21 | 1.86 | 1.74 | 1.47 |
| p-Xylene | 5.58 | 7.76 | 7.55 | 6.80 |
| m-Xylene | 12.33 | 17.15 | 16.68 | 15.02 |
| o-Xylene | 5.05 | 7.03 | 6.83 | 6.15 |
| Σ $C_8A$ | 24.17 | 33.80 | 32.80 | 29.44 |
| $C_9$ Non-aromatics | / | 0.11 | 0.12 | 0.12 |
| $C_9A$ | 2.51 | 14.56 | 20.51 | 34.02 |
| Indane | / | 0.05 | 0.05 | 0.05 |
| $C_{10}$ Hydrocarbons | 2.92 | 4.26 | 8.66 | 11.54 |

Data in the above Table were processed according to the following equations:

Toluene Conversion =

$$\frac{\text{Toluene in Feedstock} - \text{Toluene in Product Effluent}}{\text{Toluene in Feedstock}} \times 100\% \text{ (wt)}$$

$C_9A$ Conversion =

$$\frac{C_9A \text{ in Feedstock} - C_9A \text{ in Product Effluent}}{C_9A \text{ in Feedstock}} \times 100\% \text{ (wt)}$$

Indane Conversion =

$$\frac{\text{Indane in Feedstock} - \text{Indane in Product Effluent}}{\text{Indane in Feedstock}} \times 100\% \text{ (wt)}$$

Conversion of $C_9$ Non-aromatic Hydrocarbons =

$$\frac{C_9 \text{ Non-aromatic Hydrocarbons in Feedstock} - C_9 \text{ Nnon-aromatic Hydrocarbons in Product Effluent}}{C_9 \text{ Non-aromatic Hydrocarbons in Feedstock}} \times 100\% \text{ (wt)}$$

Benzene Selectivity =

$$\frac{\text{Benzene in Product Effluent} - \text{Benzene in Feedstock}}{(\text{Toluene} + C_9A) \text{ Converted in Reaction}} \times 100\% \text{ (wt)}$$

$C_8A$ Selectivity =

$$\frac{C_8A \text{ in Product Effluent} - C_8A \text{ in Feedstock}}{(\text{Toluene} + C_9A) \text{ Converted in the Reaction}} \times 100\% \text{ (wt)}$$

Results of example 15 obtained by processing the corresponding data in Table 1 were as follows:

| | |
|---|---|
| Toluene Conversion: | 39.10% |
| $C_9A$ Conversion: | 60.02% |
| Indane Conversion: | 95.55% |
| $C_9$ Non-aromatic Hydrocarbon Conversion: | 89.42% |
| Benzene Selectivity: | 20.32% |
| $C_8A$ Selectivity: | 74.63% |

As can be seen from the data in Table 1, while proportions of the different product components varied with feedstock compositions and reaction conditions, quantities of benzene and $C_8A$ increased significantly, illustrating that benzene and $C_8A$ were produced in the reaction. From the data in Table 1 and the data processing results as to example 15, it can be seen that concentrations of $C_9$ non-aromatic hydrocarbons and indane contained in the feedstock decreased substantially after reaction, illustrating that the catalyst of the present invention enjoys very good capacities of converting $C_9$ non-aromatic hydrocarbons and indane. Therefore, if an o-xylene production unit is provided in the separation flow for the product effluent of toluene disproportionation and transalkylation processes, o-xylene of high quality (purity higher than 98%) can be produced. The above examples showed that the feedstock are allowed to contain high concentrations of indane and $C_{10}$ hydrocarbons. Whereby all $C_9A$, indane and a part, or even all, of $C_{10}$ hydrocarbons may be separated from the top of the heavy aromatic hydrocarbon tower in the industrial units and $C_9A$ resource can be fully utilized. Meanwhile, since $C_{10}$ hydrocarbons in the feedstock can inhibit to a certain extent the disproportionation reaction of $C_9A$, which favors transalkylation of $C_9A$ to form $C_8A$, $C_8A$ selectivity is increased.

Therefore, high purity o-xylene can be produced from the process of the present invention, and further, more o-xylene can be produced with the same reaction feedstock consumption.

(II) Where the Aromatic Hydrocarbon Reactants Comprise Substantially Toluene and $C_{10}A$ The reactor in example 14 was used, with 20 g of a catalyst packed therein. Feedstock rich in toluene and $C_{10}A$ was mixed with hydrogen and passed through the catalyst bed from the top to the bottom to effect aromatic hydrocarbon conversion reactions. The feed toluene and $C_{10}A$ were available from hydrocarbon combination units in petrochemical industry.

Example 18~20

Catalyst A was used. The reaction conditions and results were summarized in Table 2.

TABLE 2

Reaction Conditions and Results for Feedstock Rich in Toluene and $C_{10}A$

| Example | 18 | 19 | 20 |
|---|---|---|---|
| Temperature, °C. | 350 | 390 | 470 |
| Pressure, MPa | 2.0 | 3.0 | 4.0 |
| Hydrogen/Hydrocarbon Molar Ratio | 4 | 5.5 | 10 |
| WHSV, hr$^{-1}$ | 0.5 | 1.5 | 2.5 |
| Feedstock Composition, % | | | |
| Non-aromatic Hydrocarbons | / | 0.04 | / |
| Benzene | 0.06 | 0.29 | 0.50 |
| Toluene | 10.00 | 50.32 | 88.10 |
| $C_8A$ | 0.61 | 0.91 | 1.63 |
| $C_9A$ | 7.08 | 4.04 | 1.00 |
| $C_{10}A$ | 78.48 | 41.86 | 8.52 |
| Indane | 1.00 | 0.62 | 0.12 |
| $C_{11}A$ | 3.12 | 1.92 | 0.33 |
| Product Effluent Composition, % | | | |
| Non-aromatic Hydrocarbons | 2.70 | 2.85 | 0.61 |
| Benzene | 3.50 | 7.71 | 17.72 |
| Toluene | 8.08 | 31.20 | 46.81 |
| Ethylbenzene | 2.98 | 2.27 | 0.80 |
| Xylene | 20.36 | 31.43 | 23.08 |
| Methylethylbenzene | 3.78 | 4.94 | 2.17 |
| Trimethylbenzene | 14.01 | 12.13 | 5.00 |
| $C_{10}A$ | 40.76 | 5.77 | 3.32 |
| Indane | 0.10 | 0.05 | / |
| $C_{11}A$ | 1.73 | 1.65 | 0.49 |
| Benzene + $C_8A$ | 26.84 | 41.41 | 41.60 |
| Benzene + $C_8$ + $C_9A$ | 42.63 | 58.48 | 48.77 |

Example 21~23

Catalyst B, C, and D were used. The reaction conditions and results were summarized in Table 3.

TABLE 3

Reaction Conditions and Results for Feedstock Rich in Toluene and $C_{10}A$

| Example | 21 | 22 | 23 |
|---|---|---|---|
| Catalyst Used | B | C | D |
| Temperature, °C. | 390 | 390 | 390 |
| Pressure, MPa | 3.0 | 3.0 | 3.0 |
| Hydrogen/Hydrocarbon Molar Ratio | 5.5 | 5.5 | 5.5 |
| WHSV, hr$^{-1}$ | 1.5 | 1.5 | 1.5 |
| Feedstock Composition, % | | | |
| Non-aromatic Hydrocarbons | 0.04 | 0.04 | 0.04 |
| Benzene | 0.29 | 0.29 | 0.29 |
| Toluene | 50.32 | 50.32 | 50.32 |
| $C_8A$ | 0.91 | 0.91 | 0.91 |
| $C_9A$ | 4.04 | 4.04 | 4.04 |
| $C_{10}A$ | 41.86 | 41.86 | 41.86 |
| Indane | 0.62 | 0.62 | 0.62 |
| $C_{11}A$ | 1.92 | 1.92 | 1.92 |
| Product Effluent Composition, % | | | |
| Non-aromatic Hydrocarbons | 1.85 | 2.08 | 2.36 |
| Benzene | 5.97 | 6.82 | 7.42 |
| Toluene | 34.28 | 32.76 | 31.95 |
| Ethylbenzene | 1.89 | 2.01 | 2.18 |
| Xylene | 28.31 | 30.20 | 31.05 |
| Methylethylbenzene | 4.11 | 5.17 | 5.32 |
| Trimethylbenzene | 15.56 | 13.21 | 12.35 |
| $C_{10}A$ | 5.99 | 5.74 | 5.48 |
| Indane | 0.06 | 0.05 | 0.04 |
| $C_{11}A$ | 1.98 | 1.96 | 1.85 |
| Benzene + $C_8A$ | 36.17 | 39.03 | 40.65 |
| Benzene + $C_8$~$C_9A$ | 55.84 | 57.41 | 58.32 |

The following equations were employed to process the data in Table 3:

Toluene Conversion =

$$\frac{\text{Toluene into Reactor} - \text{Toluene out from Reactor}}{\text{Toluene into Reactor}} \times 100\%$$

$C_{10}A$ Conversion =

$$\frac{C_{10}A \text{ into Reactor} - C_{10}A \text{ out from Reactor}}{C_{10}A \text{ into Reactor}} \times 100\%$$

Benzene Selectivity =

$$\frac{\text{Benzene out from Reactor} - \text{Benzene into Reactor}}{(\text{Toluene} + C_{10}A) \text{ Converted in Reaction}} \times 100\% \text{ (wt)}$$

$C_9A$ Selectivity =

$$\frac{C_9A \text{ out from Reactor} - C_9A \text{ into Reactor}}{(\text{Toluene} + C_{10}A) \text{ Converted in Reaction}} \times 100\% \text{ (wt)}$$

$C_8A$ Selectivity =

$$\frac{C_8A \text{ out from Reactor} - C_8A \text{ into Reactor}}{(\text{Toluene} + C_{10}A) \text{ Converted in Reaction}} \times 100\% \text{ (wt)}$$

Results of example 19 by processing the corresponding data of feedstock compositions and product effluent compositions in Table 3 were as follows:

| | |
|---|---|
| Toluene Conversion: | 40.78% |
| $C_{10}A$ Conversion: | 86.22% |
| Benzene Selectivity: | 12.49 wt % |
| $C_8A$ Conversion: | 55.26 wt % |
| $C_9A$ Selectivity: | 21.66 wt % |
| (Benzene + $C_8A$) Selectivity: | 67.75 wt % |
| (Benzene + $C_8$~$C_9A$) Selectivity: | 89.41 wt % |

It can be seen that the proportions of benzene, toluene, $C_8A$ and $C_9A$ in the product effluent varied with the weight ratios of toluene and $C_{10}A$ in the feedstock. Yet the following features are shared in common: (1) Both toluene and $C_{10}A$ contents decreased after reaction in all cases of different toluene to $C_{10}A$ weight ratios, demonstrating that toluene and $C_{10}A$ were converted in the reactions; (2) Benzene, $C_8A$ and $C_9A$ contents increased simultaneously in all cases of different toluene to $C_{10}A$ weight ratios, demonstrating that benzene, $C_8A$ and $C_9A$ were formed in the reactions.

It can be seen from Table 2 and the data processing results that product compositions and reaction results for disproportionation and transalkylation of toluene and $C_{10}A$ are similar to that of toluene and $C_9A$ with the same weight ratio, except that the main products are benzene, $C_8A$ and $C_9A$ for disproportionation and transalkylation of toluene and $C_{10}A$, while the main products are benzene and $C_8A$ for disproportionation and transalkylation of toluene and $C_9A$.

It can be seen from Table 2 and Table 3 that the bismuth-containing zeolite catalysts A, B, C and D of the present invention all enjoy fairly good effects in the conversion reactions of feedstock comprising substantially toluene and $C_{10}A$.

It can be seen from the examples that the process of the present invention for the disproportionation and transalkylation of toluene and $C_{10}A$ is an efficient way to produce benzene, $C_8$ and $C_9A$ from toluene and $C_{10}A$. $C_{10}A$ play substantially the same role in the process for the disproportionation and transalkylation of toluene and $C_{10}A$ as $C_9A$ in the process for the disproportionation and transalkylation of toluene and $C_9A$, i.e., $C_{10}A$ may be used to produce benzene and $C_8A$ instead of $C_9A$.

(III) Where the Aromatic Hydrocarbon Reactants Comprise Substantially Heavy Aromatic Hydrocarbons 1. Where the Heavy Aromatic Hydrocarbons Comprise Substantially $C_{10}A$ $C_{10}A$ feedstock, the composition of which is shown in Table 4, containing methylethylbenzene, trimethylbenzene, indane, diethylbenzene, dimethylethylbenzene, tetramethylbenzene, and other $C_{10}$ and $C_{11}A$, was derived from an aromatic hydrocarbons combination unit in petrochemical industry and its composition is shown in Table 4.

TABLE 4

Composition of $C_{10}A$ Feedstock

| Component | Content, wt % |
|---|---|
| Methylethylbenzene | 0.12 |
| Trimethylbenzene | 2.73 |
| Indane | 2.13 |
| Diethylbenzene | 7.79 |
| Dimethylethylbenzene | 23.32 |
| Tetramethylbenzene | 20.46 |
| Other $C_{10}A$ | 25.23 |
| $\Sigma\ C_{10}A$ | 76.80 |
| $C_{11}A$ | 18.22 |

In the $C_{10}A$ feedstock, the sum of the $C_{10}$ and $C_{11}A$ contents was 95.02%, indane content was 2.13% and $C_9A$ content was only 2.85%.

The reactor of example 14 was used, with 20 g of a catalyst packed therein. Feedstock rich in $C_9A$ and $C_{10}A$ was mixed with hydrogen and passed through the catalyst bed from the top to the bottom to effect hydrodealkylation and transalkylation reactions, in which aromatic hydrocarbons of less carbon atoms, for example, benzene, toluene, ethylbenzene, dimethylbenzene, methylethylbenzene, trimethylbenzene and the like, as well as small quantities of alkanes, for example, methane, ethane, propane, butane and the like, were produced. Hydrogen was used in this process because, on the one hand, the hydrodealkylation reactions per se consume hydrogen; on the other hand, presence of hydrogen can prolong catalyst life by inhibiting coke deposition thereon.

Example 24~27

Feedstock rich in $C_{10}A$ was subjected to hydrodealkylation and transalkylation reactions over the catalysts A to D prepared in Examples 1 to 4 respectively. The experimental results were processed according to the following equations:

$$C_6 \sim C_9 A\ \text{Yield} = \frac{C_6 \sim C_9 A\ \text{Produced}}{(C_{10} + C_{11}A)\ \text{Converted}} \times 100\%\ (\text{wt})$$

$$C_{10}A\ \text{Conversion} = \frac{C_{10}A\ \text{into Reactor} - C_{10}A\ \text{out from Reactor}}{C_{10}A\ \text{into Reactor}} \times 100\%\ (\text{wt})$$

$$C_{11}A\ \text{Conversion} = \frac{C_{11}A\ \text{into Reactor} - C_{11}A\ \text{out from Reactor}}{C_{11}A\ \text{into Reactor}} \times 100\%\ (\text{wt})$$

TABLE 5

Reaction Conditions and Results for Feedstock Rich in $C_{10}A$

| Example | 24 | 25 | 26 | 27 |
|---|---|---|---|---|
| Catalyst | A | B | C | D |
| Temperature, °C. | 350 | 370 | 380 | 450 |
| Pressure, MPa | 2.0 | 3.0 | 3.0 | 4.0 |
| Hydrogen/Hydrocarbon Molar Ratio | 3 | 10 | 5.6 | 5.6 |
| WHSV, $hr^{-1}$ | 0.5 | 1.0 | 1.5 | 2.0 |
| Product Effluent Composition, % | | | | |
| Non-aromatic Hydrocarbons | 0.80 | 1.20 | 3.10 | 6.10 |
| Benzene | 1.30 | 1.63 | 2.30 | 3.70 |
| Toluene | 7.43 | 10.05 | 9.08 | 8.07 |
| Ethylbenzene | 1.02 | 2.10 | 1.79 | 1.70 |
| Dimethylbenzene | 14.00 | 19.10 | 15.63 | 16.11 |
| Methylethylbenzene | 2.95 | 2.70 | 2.96 | 2.00 |
| Trimethylbenzene | 11.70 | 16.07 | 12.20 | 14.59 |
| Indane | 0.30 | 0.10 | 0.35 | 0.11 |
| $C_{10}A$ | 55.50 | 43.44 | 48.14 | 44.16 |
| $C_{11}A$ | 5.50 | 3.61 | 4.45 | 3.96 |
| $C_6\sim C_9A$ | 37.50 | 51.65 | 43.96 | 45.67 |
| $C_{10}A$ conversion, % | 29.8 | 46.6 | 39.5 | 46.9 |
| $C_{11}A$ conversion, % | 70.6 | 80.9 | 76.4 | 79.9 |
| $C_6\sim C_9A$ yield, wt % | 94.1 | 94.1 | 89.4 | 77.7 |

The evaluation results of catalysts A to D illustrate that catalysts comprising mordenite and a cocatalyst which comprises bismuth and one or more components selected from Fe, Co, Ni and Mo enjoy good catalytic capacities for hydrodealkylation and transalkylation reactions of $C_{10}$ and $C_{11}A$. Under preferred conditions, $C_{10}A$ conversion can reach 46.6%, $C_{11}A$ conversion can reach 80.8% and $C_6$ to $C_9A$ yield can reach up to 94.1%.

As can be seen from the product effluent composition, though $C_{11}A$ content in the feedstock was as high as 18.22%, $C_{11}A$ content in the product stream was no higher than 6%, illustrating that $C_{11}A$ undergo more readily than $C_{10}A$ hydrodealkylation and transalkylation reactions, therefore $C_{11}A$ can be used effectively in the process of the present invention for the production of $C_6$ to $C_9A$.

In the product effluents, benzene contents were significantly lower than that of toluene, $C_8A$ an $C_9A$. For example, in the product effluent of example 24, the benzene/tuluene/$C_8A/C_9A$ molar ratio was 1:3.35:5.57:4.28. The following reasons for low benzene contents are presumed: (1) Conversion of $C_{10}A$ and $C_{11}A$ to benzene required multi-step serial hydrodealkylation and transalkylation reactions, which led to little benzene generated; or (2) Benzene formed intermediately from the multi-step serial reactions, though the quantity of which might be considerable, was consumed in its transalkylation reactions with $C_{10}A$ to produce toluene and $C_9A$ as well as with $C_9A$ to produce toluene and xylene under the reaction conditions, whereby the benzene contents in the final products were significantly lower than that of toluene, $C_8A$ and $C_9A$.

No propylbenzene was detected in the product effluent. This can presumably be attributed to the facts that no propyl containing components were comprised in the feedstock, and that propylbenzene formed intermediately, the amount of which was small, underwent depropylation reactions and were consumed in its entirety.

2. Where the Heavy Aromatic Hydrocarbons Comprise Substantially $C_9A$

Example 28

Feedstock rich in $C_9A$ was passed into a reactor of example 14 with catalyst G3 packed therein, to effect reactions at a temperature of 390° C., a pressure of 1.0 MPa, a hydrogen to hydrocarbons molar ratio of 4.0, and a feedstock weight hourly space velocity of 2.0 $hr^{-1}$. The feedstock comprised 1.00 wt % of toluene, 1.30 wt % of indane, 97.0 wt % of $C_9A$, 0.70 wt % of $C_{10}A$. The product effluent comprised 2.07 wt % of benzene, 14.50 wt % of toluene, 27.14 wt % of $C_8A$, 39.07 wt % of $C_9A$, 9.85 wt % of $C_{10}A$ and 1.04 wt % of $C_{11}A$.

Data processing results were obtained in the same way as described in the previous examples.

$C_9A$ Conversion=59.8 wt %

(Toluene+$C_8A$+Benzene) Selectivity=67.9 wt %

It can be seen that catalysts of the present invention enjoy good catalytic capacities for the conversion of heavy aromatic hydrocarbons comprising substantially $C_9A$.

(IV) Where the Aromatic Hydrocarbons Comprise High Content of Water

Example 29

A series of experiments were conducted in this example.

Feedstock comprising toluene and $C_9A$ with a 60/40 molar ratio and a water content of 500 ppm, was passed into a reactor of example 14, which was packed respectively with 20 g of the bismuth containing H-ZSM-5 zeolite catalyst E of example 5, the bismuth containing β-zeolite catalyst F of example 6, the H-ZSM-5 zeolite catalyst Ec without bismuth of example 7, the β-zeolite catalyst F without bismuth of example 8, the bismuth containing high-silica mordenite catalysts of examples 9–11 and the mordenite catalyst J without bismuth of example 12, to effect reactions at a temperature of 385° C., a pressure of 3.0 MPa(gauge), a hydrogen to hydrocarbons molar ratio of 5 and a feedstock weight hourly space velocity of 1.5 $hr^{-1}$. Experimental results were summarized in Table 6.

As is shown in Table 6, all of the catalysts of the present invention, whether in which bismuth was added by kneading or impregnating with an aqueous bismuth solution, demonstrate good activities and selectivity, especially enjoy much higher $C_9A$ conversion capacities than the comparative catalyst J without bismuth. Even among catalysts in which the zeolite used were aluminum-lean mordenites, those containing bismuth enjoy higher activities than those without bismuth.

As is also shown in Table 6, the ZSM-5-zeolite and β-zeolite catalysts containing bismuth demonstrate higher C9A conversion capacities than their counterparts without bismuth. These experiments illustrate that bismuth contained in the catalysts of the present invention is a basic factor contributing to their distinguished performances.

Example 30

Further experiments were conducted over catalyst G3 of example 9 and catalyst J of example 12 to evaluate their stability. The reactor and reaction conditions of example 29 were used, except that initial reaction temperatures for catalysts G3 and J, respectively, were 380° C. and 400° C., and that $C_9A$ conversion was maintained at about 45 mol % by elevating the reaction temperatures gradually. Experimental results were summarized in Table 7. For catalyst G3 of the present invention, during a reaction cycle of 1000 hours with a mean $C_9A$ conversion of 45.2% and a mean ($C_8A$+Benzene) selectivity of 96.1 mol %, reaction temperature was elevated from the initial of 380° C. to the final of 395° C.; while for the comparative catalyst J, in a reaction cycle of 500 hours with a mean $C_9A$ conversion of 45.1% and a mean ($C_8A$+Benzene) selectivity of 96.0%, reaction temperature was elevated from the initial of 400° C. to the final of 460° C. Thus it can be seen that the catalysts of the present invention are fit for reactants with a high water content, i.e., enjoy high water resistance in addition to their high activities, selectivity and stability.

TABLE 6

Evaluation Results for Catalyst Activity

| No. | Zeolite Form | $SiO_2/Al_2O_3$ Molar Ratio | Zeolite/ Alumina Weight Ratio | $Bi_2O_3$, wt % | Bismuth Adding Method | $C_9A$ Conversion, mol % | Benzene + $C_8A$ Selectivity, mol % |
|---|---|---|---|---|---|---|---|
| G1 | H-Mordenite | 18.1 | 50/50 | 0.1 | Kneading | 43.2 | 96.5 |
| G2 | H-Mordenite | 15.3 | 50/50 | 0.5 | Kneading | 45.2 | 96.0 |
| G3 | H-Mordenite | 24.0 | 50/50 | 1.0 | Kneading | 46.3 | 94.7 |
| G4 | H-Mordenite | 25.1 | 50/50 | 5.0 | Kneading | 48.4 | 93.2 |
| G5 | H-Mordenite | 27.0 | 70/30 | 0.1 | Kneading | 44.0 | 96.5 |
| G6 | H-Mordenite | 31.2 | 30/70 | 0.1 | Kneading | 40.1 | 95.0 |
| H1 | H-Mordenite | 18.1 | 50/50 | 0.1 | Impregnating | 42.9 | 96.6 |
| H2 | H-Mordenite | 24.0 | 50/50 | 1.0 | Impregnating | 46.1 | 94.4 |
| H3 | H-Mordenite | 27.0 | 70/30 | 0.1 | Impregnating | 44.3 | 96.2 |
| H4 | H-Mordenite | 15.3 | 70/30 | 1.0 | Impregnating | 46.4 | 94.4 |
| H5 | H-Mordenite | 25.1 | 60/40 | 10.0 | Impregnating | 48.2 | 91.3 |
| I1 | Aluminum- | 15.1 | 50/50 | 1.0 | Kneading | 37.6 | 95.0 |
| I2 | lean | 19.8 | 50/50 | 1.0 | Kneading | 38.1 | 95.4 |
| I3 | Mordenite | 24.9 | 50/50 | 1.0 | Kneading | 34.5 | 93.8 |
| J | H-Mordenite | — | 50/50 | 0 | — | 33.0 | 96.9 |
| E | ZSM-5-zoelite | 65 | 70/30 | 1.0 | Kneading | 40.8 | 96.1 |
| F | β-zeolite | 35 | 70/30 | 1.0 | Kneading | 40.0 | 95.6 |
| Ec | ZSM-5-zeolite | 65 | 70/30 | 0 | — | 36.6 | 96.7 |
| Fc | β-zeolite | 35 | 70/30 | 0 | — | 35.8 | 96.2 |

TABLE 7

Stability of Catalyst G3 of the Present Invention and Comparative Catalyst J

| Catalyst | Reaction Time, hrs | Reaction Temperature, °C. Initial → Final | Mean $C_9A$ Conversion, mol % | Mean ($C_8A$ + Benzene) Selectivity, mol % |
|---|---|---|---|---|
| G3 | 1000 | 380 → 395 | 45.2 | 96.1 |
| J | 500 | 400 → 460 | 45.2 | 96.0 |

Example 31

Experiments were conducted, using the reactor and reaction conditions of example 29, except that catalysts K1 to K5 of example 13 were packed in respectively, to evaluate their activities. Experimental results were summarized in Table 8.

TABLE 8

Evaluation Results for Catalyst Activities[#]

| Catalyst | | | | | | $C_9A$ Conversion, | Benzene + $C_8$ Selectivity, |
|---|---|---|---|---|---|---|---|
| No. | CuO | $La_2O_3$ | $Zr_2O_3$ | $Re_2O_3$ | SrO | $Bi_2O_3$ | mol % | mol % |
| K1 | — | 1.0 | — | — | — | 0.2 | 44.0 | 96.3 |
| K2 | 5.0 | — | — | — | — | 0.5 | 47.0 | 94.2 |
| K3 | — | 0.1 | 0.3 | — | — | 1.0 | 45.2 | 96.4 |
| K4 | — | — | — | 0.15 | — | 1.0 | 46.8 | 93.9 |
| K5 | — | — | — | — | 0.3 | 5.0 | 48.0 | 93.1 |

Note[#]: Mordenite: $SiO_2/Al_2O_3$ = 27.0 mol/mol; weight ratio of mordenite to alumina = 70/30

Data in Table 8 demonstrate that the mordenite catalysts with, supported thereon, $Bi_2O_3$ and one or more optional components selected from CuO, $La_2O_3$, $Zr_2O_3$, $Re_2O_3$ and SrO, all enjoy high $C_9A$ conversion and (benzene+$C_8A$) selectivity, i.e., enjoy high catalytic performances.

The above examples are for the purposes of illustration only and shall not constitute limits to the present invention. It is to be understood by those skilled in the art that any variation and modification of the above embodiments fall within the scope of the appended claims.

What is claimed is:

1. A catalyst for the disproportionation and transalkylation reactions of toluene and heavy aromatic hydrocarbons including $C_9A$ and $C_{10}A$, and/or the hydrodealkylation and/or transalkylation reactions of heavy aromatic hydrocarbons including $C_9A$ and $C_{10}A$, consisting of by weight 20 to 90 parts of mordenite or β-zeolite having a $SiO_2/Al_2O_3$ molar ratio of about 15.1 to 27.0, about 0.05 to 1.0 parts of metal bismuth or oxides thereof supported on the zeolite, 0 to 5 parts of one or more metal(s) M or oxides thereof, M being selected from the group consisting of molybdenum, copper, strontium, lanthanum, and rhenium, and 10 to 60 parts of alumina as an adhesive.

2. A catalyst according to claim 1, wherein said zeolite is hydrogen-form mordenite.

3. A catalyst according to claim 1, wherein the content of said metal bismuth or oxide thereof is within the range of 0.1 to 1.0 parts by weight.

4. A process for the conversion of aromatic hydrocarbons, comprising contacting said aromatic hydrocarbon feedstock with a catalyst according to claim 1 to effect conversion reactions under conversion conditions.

5. A process for the conversion of aromatic hydrocarbons according to claim 4, comprising passing said aromatic hydrocarbon feedstock through a gas-solid fixed-bed reactor and contacting said aromatic hydrocarbon feedstock with the catalyst inside the reactor in the presence of hydrogen to effect conversion reactions.

6. A process for the conversion of aromatic hydrocarbons according to claim 5, wherein said conversion reactions are carried out at a reaction temperature within the range from 300 to 600° C., a reaction pressure within the range from 1.5 to 4.0 MPa, a feedstock weight hourly space velocity within the range from 0.5 to 3.0 $hr^{-1}$, and a molar ratio of hydrogen to hydrocarbons within the range from 2 to 10.

7. A process for the conversion of aromatic hydrocarbons according to claim 1, wherein the water content in said aromatic hydrocarbon feedstock is within the range from 0 to 500 ppm.

8. A process for the conversion of aromatic hydrocarbons according to claim 1, wherein the indane content in said aromatic hydrocarbon feedstock is within the range from 0 to 5 wt %.

9. A process for the conversion of aromatic hydrocarbons according to claim 1, wherein said aromatic hydrocarbon feedstock comprises substantially toluene and $C_9A$.

10. A process for the conversion of aromatic hydrocarbons according to claim 1, wherein said aromatic hydrocarbon feedstock comprises substantially toluene, $C_{10}A$ and heavy aromatic hydrocarbons of more than ten carbon atoms.

11. A process for the conversion of aromatic hydrocarbons according to claim 1, wherein said aromatic hydrocarbon feedstock comprises substantially $C_9A$, $C_{10}A$, heavy aromatic hydrocarbons of more than ten carbon atoms or a mixture of two or more types of aromatic hydrocarbons selected therefrom.

12. A process for the conversion of aromatic hydrocarbons comprising the following steps of:
   (a) separating an aromatic hydrocarbon feedstock comprising indane, $C_8$ aromatic hydrocarbons ($C_8A$), $C_9A$, $C_{10}A$ and $C_{11}$ aromatic hydrocarbons ($C_{11}A$) in a first separation zone comprising a first and a second separation tower, where a stream rich in $C_8A$ is separated from the top of the first separation tower and the bottoms product of the first tower is passed into the second separation tower, where a stream comprising indane, $C_9A$ and $C_{10}A$, with an indane content of 0 to 5 wt % and a $C_{10}A$ content of 0 to 50 wt %, is separated from the top of the second separation tower and $C_{11}A$ are removed from the second tower bottom;

(b) passing the effluent stream from the top of the second separation tower along with toluene into a conversion reaction zone for the aromatic hydrocarbons, where said reaction zone is packed with a catalyst according to any one of claims 1 to 3, and the aromatic hydrocarbons are transformed, upon contacting the catalyst under conversion conditions, into a converted effluent rich in benzene and $C_8A$; and (c) passing said converted effluent into a second separation zone and separating them into benzene, toluene, $C_8A$ and heavy aromatic hydrocarbons containing $C_{10}A$.

13. A process for the conversion of aromatic hydrocarbons according to claim 12, wherein toluene separated from the second separation zone is recycled and fed into the conversion reaction zone.

14. A process for the conversion of aromatic hydrocarbons according to claim 12, wherein the heavy aromatic hydrocarbons comprising $C_{10}A$ separated from the second separation zone are passed into the second separation tower of the first separation zone.

15. A process for the conversion of aromatic hydrocarbons according to claim 12, wherein the heavy aromatic hydrocarbons comprising $C_{10}A$ separated from the second separation zone, after first separated therefrom o-xylene, is then passed into the second separation tower of the first separation zone.

* * * * *